United States Patent
Min et al.

(10) Patent No.: US 9,387,325 B1
(45) Date of Patent: Jul. 12, 2016

(54) SYSTEM AND METHOD TO CONTROL DORSAL ROOT STIMULATION PARAMETERS BASED ON FREQUENCY DECOMPOSITION

(71) Applicant: PACESETTER, INC., Sylmar, CA (US)

(72) Inventors: Xiaoyi Min, Camarillo, CA (US); Melanie Goodman Keiser, McKinney, TX (US); Wenbo Hou, Santa Clarita, CA (US); Bruce A. Morley, Garland, TX (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 14/577,933

(22) Filed: Dec. 19, 2014

(51) Int. Cl.
  *A61N 1/00* (2006.01)
  *A61N 1/36* (2006.01)
  *A61N 1/05* (2006.01)

(52) U.S. Cl.
  CPC .......... *A61N 1/36139* (2013.01); *A61N 1/3615* (2013.01); *A61N 1/36071* (2013.01); *A61N 1/36171* (2013.01); *A61N 1/36178* (2013.01); *A61N 1/0551* (2013.01)

(58) Field of Classification Search
  CPC ........... A61N 1/36171; A61N 1/36071; A61N 1/0551; A61N 1/139; A61N 1/3615; A61N 1/36178
  See application file for complete search history.

(56) References Cited

U.S. PATENT DOCUMENTS

| | | | |
|---|---|---|---|
| 5,188,104 A * | 2/1993 | Wernicke et al. | 607/40 |
| 6,208,902 B1 * | 3/2001 | Boveja | 607/46 |
| 8,620,425 B2 * | 12/2013 | Zhou et al. | 607/9 |

OTHER PUBLICATIONS

Koga, Kohei et al., "Selective activation of primary afferent fibers evaluated by sine-wave electrical stimulation," Molecular Pain. 2005;1(13)1744-8069.
Sundar, Swarna et al., "On the Activation Threshold of Nerve Fibers Using Sinusoidal Electrical Stimulation," Proceedings of the 28th IEEE (EMBS Annual Intern'l Conf—NYC, USA). Aug. 30-Sep. 3, 2006;2908-2911.

* cited by examiner

*Primary Examiner* — George Manuel

(57) ABSTRACT

A system and method are provided for controlling stimulation of nervous tissue of a patient. The method comprises delivering a stimulation waveform to at least one electrode located proximate to nervous tissue of interest, the stimulation waveform including a series of pulses configured to excite at least one of A-beta (Aβ) fibers, A-delta (Aδ) fibers or C-fibers of the nervous tissue of interest, the stimulation waveform defined by therapy parameters. The method also provides sensing an evoked compound action potential (ECAP) signal from the nervous tissue of interest. The method also analyzes a frequency content of the ECAP signal to obtain ECAP frequency data indicative of activity by at least one type of nerve fibers from a group comprising Aβ, Aδ and C fibers. The method also determines the type of nerve fibers that were activated by the stimulation waveform based on the ECAP frequency data.

10 Claims, 8 Drawing Sheets

SYSTEM AND METHOD TO CONTROL DORSAL ROOT STIMULATION PARAMETERS BASED ON FREQUENCY DECOMPOSITION

FIELD OF THE INVENTION

Embodiments of the present disclosure generally relate to neurostimulation (NS), and more particularly to determining activity of different types of nerve fibers based on frequency domain analysis.

BACKGROUND OF THE INVENTION

Spinal cord stimulation (SCS) is used to treat a wide range of chronic neuropathic pain conditions by delivering electrical stimulation to select portions of the spinal cord. In the past, SCS therapy has been proposed in which a therapy is defined by one or more pulses have a select pulse width, frequency and intensity. The pulse width, frequency and intensity may be changed, along with electrode configuration and placement on the spinal column in connection with pain relief for individual patients.

NS systems are devices that generate electrical pulses and deliver the pulses to nervous tissue to treat a variety of disorders. For example, spinal cord stimulation has been used to treat chronic and intractable pain. The application of electrical pulses to certain regions or areas of nervous tissue can effectively reduce the number of pain signals that reach the brain. SCS therapy, delivered via epidurally implanted electrodes, is a widely used treatment for chronic intractable neuropathic pain of different origins. Applying electrical energy to the spinal cord associated with regions of the body afflicted with chronic pain can induce "paresthesia" (a subjective sensation of numbness or tingling) in the afflicted bodily regions. Traditional tonic therapy evokes paresthesia covering painful areas of a patient. During SCS therapy calibration, the paresthesia is identified and localized to the painful areas by the patient.

Stimulation of the dorsal root ganglion (DRG) has shown promising clinical results in managing chronic pain in targeted anatomy such as the foot, groin and phantom limb and other peripheral neuropathies. By stimulating the DRG, therapy can be adjusted to cover either broad or specific areas of pain throughout the torso and legs, while limiting uncomfortable postural effects typically experienced with traditional SCS.

A need remains for improved methods and systems for managing stimulation parameters in connection with targeting stimulation of select types of nerve fibers.

SUMMARY

In accordance with one embodiment, a method is provided to control stimulation of nervous tissue of a patient. The method comprises delivering a stimulation waveform to at least one electrode located proximate to nervous tissue of interest, the stimulation waveform including a series of pulses configured to excite at least one of A-beta or A-delta fibers or C-fibers of the nervous tissue of interest, the stimulation waveform defined by therapy parameters. The method also comprises sensing an evoked compound action potential (ECAP) signal from the nervous tissue of interest. The method also comprises analyzing a frequency content of the ECAP signal to obtain ECAP frequency data indicative of activity by at least one type of nerve fibers from a group comprising A$\beta$, A$\delta$ and C fibers. The method also comprises determining the type of nerve fibers that were activated by the stimulation waveform based on the ECAP frequency data.

Optionally, the ECAP frequency data may include A$\beta$, A$\delta$ and C fiber components, where the determining operation identifies an amount of activity exhibited by at least one of the A$\beta$, A$\delta$ and C fiber components in response to the stimulation waveform. Alternatively, the method may include the analyzing operation including using a fast Fourier transform to convert the time domain of ECAP signal to a frequency domain, the ECAP frequency data including clusters of frequency domain components distributed along a frequency spectrum, where each of the clusters is associated with one of the A$\beta$, A$\delta$ and C nerve fibers' activity.

Optionally, the method may include the ECAP signal representing ECAP recorded activity from afferent neurons carrying both painful stimuli, within the A$\delta$ and C fibers, and non-painful stimuli, within the A$\beta$ fibers. Alternatively, the method may further comprise adjusting at least one of the therapy parameters to change the stimulation waveform based on the ECAP frequency data.

Optionally, the method may include the adjusting operation selecting between a burst, high frequency, tonic or random pattern stimulation waveforms based upon which of the burst, high frequency, tonic or random pattern stimulation waveforms results in a selected level of activation for a target one or more of the A$\beta$, A$\delta$ or C fibers. Alternatively, the method may include the analyzing operation using a fast Fourier transform on the ECAP signals to define clusters of frequency domain components within the ECAP frequency data, the adjusting operation adjusting the stimulation parameters based on the clusters of frequency domain components to maintain a select amount of activation of a select one or more of the types of nerve fibers.

Optionally, the method may further comprise defining thresholds for activating at least one of the A$\beta$, A$\delta$ or C fibers based on the ECAP frequency data and the stimulation waveform. Alternatively, the method may include the stimulation waveform being delivered with a collection of test pulses having at least one of different amplitudes and pulse widths, the method further comprising establishing thresholds in connection with excitation of the A$\beta$, A$\delta$ or C fibers based on first detection of frequency domain components in the ECAP frequency data indicating activity of the corresponding A$\beta$, A$\delta$ or C fibers. Optionally, the method may include the therapy parameters defining at least one of a burst stimulation waveform or a high frequency stimulation waveform.

In accordance with an embodiment, a system is provided to control stimulation of nervous tissue of a patient. The system comprises a lead having at least one stimulation electrode, the lead being configured to be implanted at a target position proximate to nervous tissue of interest. The system also comprises an implantable pulse generator (IPG) coupled to the lead. The IPG is configured to deliver a stimulation waveform to at least one electrode located proximate to nervous tissue of interest, the stimulation waveform including a series of pulses configured to excite at least one of A-beta or A-delta fibers or C-fibers of the nervous tissue of interest, the stimulation waveform being defined by therapy parameters. The IPG is also configured to sense an evoked compound action potential (ECAP) signal from the nervous tissue of interest. The IPG is also configured to analyze a frequency content of the ECAP signal to obtain ECAP frequency data indicative of activity by at least one type of nerve fibers from a group comprising A$\beta$, A$\delta$ and C fibers; and determine the type of nerve fibers that were activated by the stimulation waveform based on the ECAP frequency data.

Alternatively, the system may include the IPG further comprising a processor using a fast Fourier transform to convert the ECAP signal to a frequency domain when analyzing the frequency content, the ECAP frequency data including clusters of frequency domain components distributed along a frequency spectrum, where each of the clusters is associated with one of the Aβ, Aδ and C nerve fibers. Optionally, the system may include the ECAP signal representing ECAP recorded activity from afferent neurons carrying both painful stimuli, within the Aδ and C fibers, and non-painful stimuli, within the Aβ fibers.

Alternatively, the system may include the IPG further comprising a processor operated to adjust at least one of the therapy parameters to change the stimulation waveform based on the ECAP frequency data. Optionally, the system may include the IPG further comprising a processor operated to select between a burst, high frequency, tonic or random pattern stimulation waveforms based upon which of the burst, high frequency, tonic or random pattern stimulation waveforms results in a selected level of activation for a target one or more of the Aβ, Aδ or C fibers. Alternatively, the system may include the IPG further comprising a processor that analyzes the frequency content uses a fast Fourier transform to convert the ECAP signals to a frequency domain that includes clusters of frequency domain components within the ECAP frequency data, the processor adjusting the stimulation parameters based on the clusters of frequency domain components to maintain a select amount of activation of a select one or more of the types of nerve fibers.

Optionally, the system may include the IPG further comprising a processor operated to define thresholds for activating at least one of the Aβ, Aδ or C fibers based on the ECAP frequency data and the stimulation waveform. Alternatively, the system may include the stimulation waveform being delivered with a collection of test pulses having at least one of different amplitudes and pulse widths, the IPG further comprises a processing algorithm to establish thresholds in connection with excitation of the Aβ, Aδ or C fibers based on first detection of frequency domain components in the ECAP frequency data indicating activity of the corresponding Aβ, Aδ or C fibers. Optionally, the system may include the therapy parameters defining at least one of a burst stimulation waveform or a high frequency stimulation waveform. Optionally, the system may include the algorithms to utilize the frequency results and thresholds to guide programming.

DETAILED DESCRIPTION

Figure 1:
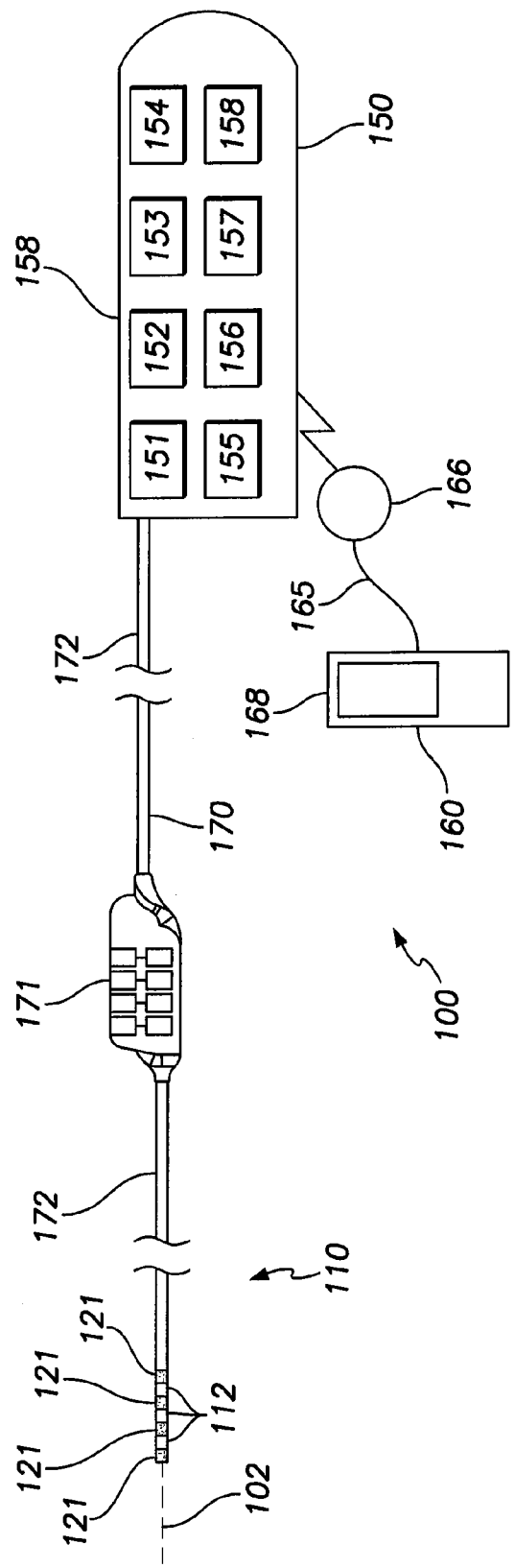
FIG. 1 illustrates a neurostimulation system that generates electrical pulses for application to tissue of a patient according to some embodiments.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

In accordance with embodiments herein, alternative ECAP (evoked compound action potential) recording sites are utilized to provide insight into activation of both painful and non-painful afferents. In accordance with embodiments herein, measurement of ECAP signals from the DRG are utilized for feedback control of stimulation parameters. The ECAP signal measurements are analyzed in the frequency domain to differentiate whether Aβ, Aδ, and C fibers are stimulated. The benefits of recording ECAP signals from electrodes located proximate to the dorsal root (DR) or dorsal root ganglia (DRG) are multi-fold including bringing the recording electrode closer to the relevant neurons, reducing posture/motion effects upon recorded ECAP signals and lowing power consumption utilized in connection with stimulation and sensing, thereby improving battery longevity.

The ECAP signals, from DR or DRG stimulation, are recorded from an electrode array. A Fast Fourier Transform (FFT) of the ECAP signal is performed and stored. In one embodiment, the afferent leads are used for stimulation and sensing. In another embodiment, the same lead or lead configuration is used for both stimulation and recording.

In one embodiment, the FFT of the ECAP signals (or FFT of sensory action potential (SAP) signals) recorded from the dorsal root or DRG are used to adjust stimulation parameter settings such as pulse width, waveforms, amplitude, pattern, tonic or burst etc. Using frequency distribution/clusters as a guide, settings may be adjusted manually or automatically in a closed-loop system. The stimulation parameters may be adjusted to maintain sufficient activation of the preferred fiber type(s), while minimizing activation of other fiber types, by using frequency domain information as discussed herein.

In some embodiments, methods and systems are provided to determine the stimulation parameters such as pulse frequency and pulse amplitudes associated with the frequency components for each nerve fiber type. In accordance herewith, test pulses are delivered and the responsive ECAP signals are recorded and analyzed to establish the thresholds. Maximum levels of stimulation amplitudes or pulse widths could be defined based on first detection of frequency components in the range indicating activated Aδ or C fibers, which is the threshold associated with pain produced by over stimulation side effects, when the stimulation amplitude is tested from low to high. The same method may be used to detect the stimulation threshold of pulse amplitude or pulse width for Aβ fibers. However, the stimulation of Aβ fibers generates paresthesia which is different from those of Aδ or C fibers.

In some embodiments, the stimulation threshold of pulse amplitude or pulse width levels may be defined according to the reduction of frequency components/size in the cluster range for Aβ fibers frequency domains, if the stimulation pulse amplitude is tested from high to low or pulse width is tested from wide to narrow.

In accordance with embodiments herein, methods and systems utilize analysis of the frequency distribution and content associated with SAP and ECAP signals, in order to enable the stimulation parameters to be tailored to fit the individual patient with burst, high-frequency or a random pattern that achieves a desired level of efficacy (e.g. maximizes the therapeutic window between desired activation of Aβ and undesired activation of Aδ or C fibers).

Nervous System Overview

The nervous system is comprised of the central nervous system (CNS) and the peripheral nervous system (PNS). The CNS contains the brain and spinal cord. The PNS is comprised mainly of mixed nerves, which are enclosed bundles of the long fibers or axons (endings of nerve cells or neurons) that connect the CNS to every other part of the body. Sensory nerve fibers represent afferent fibers that send information towards the brain, while motor nerve fibers represent efferent fibers that send information from the brain. Sensory neurons transmit information from the environment, such as pain and motor neurons that mediate voluntary and involuntary movement.

In general, the peripheral nerve fibers may be classified into various types of nerve fibers based on the nerve fiber diameter and conduction velocity, for example A, B and C-fibers. A-fibers have large diameters, high conduction velocities, are highly myelinated, and are further subdivided by size and conduction velocity as A-alpha, A-beta, A-gamma and A-delta fibers. B-fibers have diameters of about 3 um and conduction velocities of 3-15 m/s. C-fibers are small neurons with slow conduction velocities and are not myelinated.

The diameters of Aβ are in the range of 6-12 μm, Aδ is in 1-5 μm and C in 0.02-1.5 μm. The conduction velocities also differ largely from 35-75 m/s for Aβ fibers, 5-30 m/s for Aδ fibers, 0.5-2 m/s for C fibers. Aδ fibers carry information mainly from the nociceptive-mechanical or mechanothermal-specific stimuli and are considered nociceptors. Their receptive fields (area of innervation) are small, and therefore, provide precise localization of pain.

C-fibers are unmyelinated, have a small diameter and low conduction velocity. C-fibers carry sensory information, such as nociception (pain), temperature, and itch. C-fibers are unmyelinated unlike most other fibers in the nervous system. The lack of myelination is, at least in part, a cause of the slow conduction velocity attributed to C-fibers.

C-fibers are activated by and carry information from a variety of high-intensity mechanical, chemical and thermal stimulation and thus are considered as polymodal nociceptors. C-fibers comprise about 70% of all the fibers carrying noxious input. The receptive field of these neurons is large and, therefore, less precise for pain localization.

The cell bodies of all primary afferent pain neurons from the body, face, and head are located in the dorsal root ganglia and in the trigeminal ganglia respectively. Some of these cell bodies have myelinated axons (A-delta fibers), and others have unmyelinated axons (C-fibers). Both Aδ fiber's and the unmyelinated C-fiber's axons have free nerve endings, which innervate the same areas in the periphery. Aδ fibers are responsible for the sensation of a quick shallow pain that is specific on one area, termed as first pain. The Aδ fibers respond to a weaker intensity of noxious stimulus. C-fibers respond to noxious stimuli which have stronger intensities and account for the slow, but deeper second pain that spreads out over an unspecific area.

Nociception is the response to painful stimuli transmitted via sensory action potentials of Aδ and C-fibers. SCS therapy may decrease the frequency of the nociceptive action potentials with varying efficacy as the therapy parameters change. Burst and high frequency type SCS therapies can be controlled by adjusting relevant parameters to modulate the charge delivered to the spinal cord during stimulation. As explained herein, the efficacy of burst and high frequency waveform stimulations may be dependent on certain therapy parameters, more so than other therapy parameters (e.g. dependent on the charge per burst).

The spinal cord contains two distinct sensory pathways for painful and non-painful stimuli, both of which enter the spinal cord via the dorsal root. The cell bodies of the first-order afferent fibers, including Aβ, Aδ, C, are located in the dorsal root ganglia (DRG). Non-painful information is carried from mechanosensory receptors by axons of Aβ (A-Beta) neurons through the dorsal root, ascending ipsilaterally on the dorsal column, and synapsing on neurons in the dorsal column nuclei in the medulla (cuneate and gracile nuclei). Conversely, painful stimuli are carried on Aδ (A-Delta) fibers (fast pain) and C fibers (slow pain) through the dorsal root, with the fibers then branching into ascending and descending collaterals (dorsolateral tract of Lissauer), and running 1-2 spinal segments before penetrating gray matter in the dorsal horn. Subsequently, these fibers synapse on second-order neurons that ascend to the brainstem and thalamus via the anterolateral tract in the contralateral spinal cord.

Figure 3:
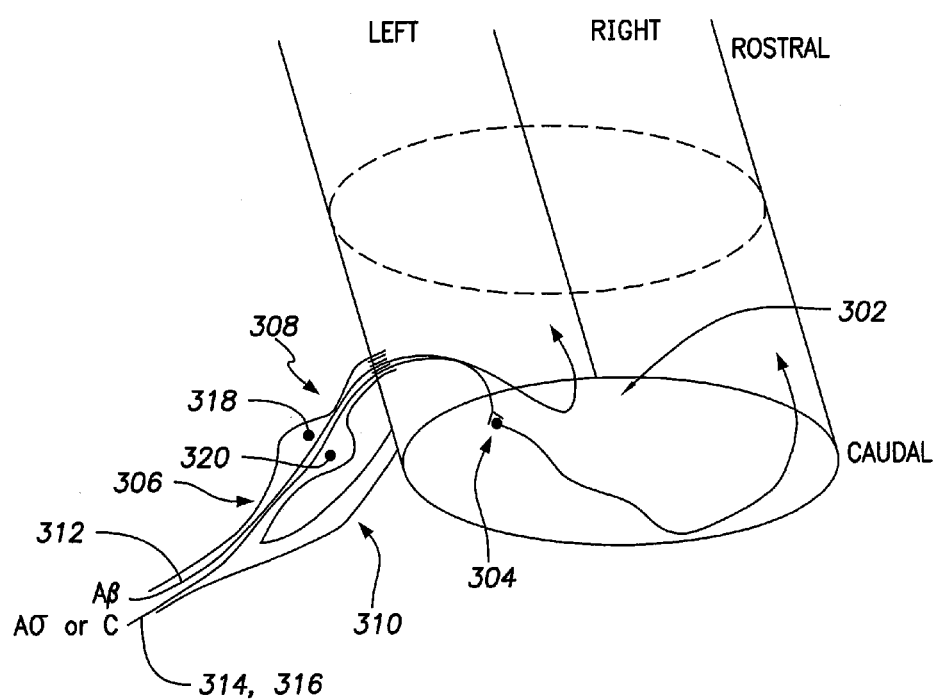
FIG. 3 illustrates a graphical representation of sensory pathways in the spinal cord in accordance with embodiments herein.

FIG. 3 illustrates a graphical representation of sensory pathways in the spinal cord. FIG. 3 illustrates the dorsal column 302. The spinal nerve branches into the dorsal root 306 and ventral root 310. The dorsal root ganglia 308 are the cell bodies of the spinal nerve 312. The DRG 308 represents a cluster or ganglion of nerve cell bodies that enter the spinal column at the dorsal horn 304. The DRG 308 includes various nerve fibers, such as Aβ fibers 312, Aδ fibers 314 and C fibers 316. Non-painful stimuli originating from mechanosensory fibers are transmitted via Aβ fibers 312 through the dorsal root 306, with cell bodies in the DRG 308, and then ascending ipsilaterally via the dorsal column 302. These neurons terminate in the gracile and cuneate nuclei in the medulla. Painful stimuli originating from pain receptors are also transmitted through the dorsal root by Aδ and C fibers, 314, 316 with cell bodies in the DRG 308, before synapsing on second-order neurons in the dorsal horn (pathway shown in blue). The second-order neurons travel contralaterally via the anterolateral tract to the brainstem and thalamus.

In accordance with embodiments herein, a lead having one or more electrodes is located proximate to the DRG 308. For example, electrodes may be positioned as denoted at 318 and 320. The electrodes 318, 320 may be utilized in connection with delivering stimulation waveforms and/or sensing ECAP and/or SAP signals, among other things. As illustrated in FIG. 3, DRG or DR have Aβ or Aδ/C fibers 312-316 close to each other. During stimulation pulse delivery, both types of nerve fibers can be activated when the stimulation strength is high enough.

Given that the fibers 312-316 may fire at different times, the ECAP signals from Aβ, Aδ and C fibers 312-316 may be superposed upon one another such that timing of propagation is difficult to differentiate when analyzing ECAP signals in the time domain. In accordance with embodiments herein, the sensed ECAP signals are converted to the frequency domain, such as utilizing a Fast Fourier Transform (FFT), in order that the frequency domain components can be individually analyzed to identify what types of fibers were activated among Aβ, Aδ and C fibers during DC, DR or DRG stimulation. The frequency components of ECAPs for Aβ, Aδ and C separate along the frequency spectrum into clusters with different frequency domain components due to the difference in the velocities, at which action potentials propagate along the corresponding nerve fibers. Activation of different fiber types are distinguished in ECAP signals sensed at the DR or DRG based on the frequency domain components, instead of latency of the corresponding ECAP signal response in the time domain. The frequency domain analysis described herein distinguishes activity within the various types of nerve fibers.

System Overview

FIG. 1 depicts an NS system 100 that generates electrical pulses for application to tissue of a patient according to some embodiments. For example, the NS system 100 may be adapted to stimulate spinal cord tissue, peripheral nervous tissue, deep brain tissue, cortical tissue, cardiac tissue, digestive tissue, pelvic floor tissue, or any other suitable nervous tissue of interest within a patient's body. The NS system 100 may be controlled to deliver various types of therapy, such as high frequency neurostimulation therapies, burst neurostimulation therapies, tonic therapy, random pattern therapy and the like. High frequency neurostimulation includes a continuous series of monophasic or biphasic pulses that are delivered at a predetermined frequency (such as 2-10 KHz). Burst neurostimulation includes short sequences of monophasic or biphasic pulses, where each sequence is separated by a quiescent period. By way of example, the pulses within each burst sequence may be delivered with an intraburst frequency of about 500 Hz.

The NS system 100 may represent a closed loop neurostimulation device, where the NS device 100 is configured to provide real-time sensing functions evoked compound action potential (ECAP) signals from a dorsal root ganglion lead. The configuration of the lead sensing electrodes that sense ECAP signals from the Aδ and C fibers may be varied depending on the neuronal anatomy of the sensing site(s) of interest. The size and shape of electrodes is varied based on the implant location, such as the dorsal root or DRG. By way of example only, a laminectomy procedure may be used, in order to obtain accurate action potential signals indicative of pain from the C fiber and/or the Aδ fiber. The electronic components within the NS system 100 are designed with both stimulation and sensing capabilities, including alternative stimulation therapy, such as burst mode, high frequency mode and the like. The NS system 100 detects an amount of activity associated with each type of nerve fiber based on the frequency content of the ECAP signals. Changes to the frequency content of the ECAP signals is used to guide parameter settings for the stimulation therapy, such as to define burst or high frequency parameters. In one embodiment, one lead stimulates the dorsal column, and a second lead senses from the DRG or DR. In another embodiment, the same lead can stimulate at the DRG or DR and sense from the same stimulation location.

The NS system 100 includes an implantable pulse generator (IPG) 150 that is adapted to generate electrical pulses for application to tissue of a patient. The IPG 150 typically comprises a metallic housing or can 158 that encloses a controller 151, pulse generating circuitry 152, a charging coil 153, a battery 154, a far-field and/or near field communication circuitry 155, battery charging circuitry 156, switching circuitry 157, memory 158 and the like. The controller 151 typically includes a microcontroller or other suitable processor for controlling the various other components of the device. Software code is typically stored in memory of the IPG 150 for execution by the microcontroller or processor to control the various components of the device.

The IPG 150 may comprise a separate or an attached extension component 170. If the extension component 170 is a separate component, the extension component 170 may connect with the "header" portion of the IPG 150 as is known in the art. If the extension component 170 is integrated with the IPG 150, internal electrical connections may be made through respective conductive components. Within the IPG 150, electrical pulses are generated by the pulse generating circuitry 152 and are provided to the switching circuitry 157. The switching circuitry 157 connects to outputs of the IPG 150. Electrical connectors (e.g., "Bal-Seal" connectors) within the connector portion 171 of the extension component 170 or within the IPG header may be employed to conduct various stimulation pulses. The terminals of one or more leads 110 are inserted within connector portion 171 or within the IPG header for electrical connection with respective connectors. The lead 110 has at least one stimulation electrode 121. The lead 110 is configured to be implanted at a target position proximate to nervous tissue of interest. The IPG 150 is coupled to the lead 110, thereby the pulses originating from the IPG 150 are provided to the leads 110. The pulses are then conducted through the conductors of the lead 110 and applied to tissue of a patient via stimulation electrodes 121 that are coupled to blocking capacitors. Any suitable known or later developed design may be employed for connector portion 171.

The stimulation electrodes 121 may be positioned along a horizontal axis 102 of the lead 110, and are angularly positioned about the horizontal axis 102 so the stimulation electrodes 121 do not overlap. The stimulation electrodes 121 may be in the shape of a ring such that each stimulation electrode 121 continuously covers the circumference of the exterior surface of the lead 110. Each of the stimulation electrodes 121 are separated by non-conducting rings 112, which electrically isolate each stimulation electrode 121 from an adjacent stimulation electrode 121. The non-conducting rings 112 may include one or more insulative materials and/or biocompatible materials to allow the lead 110 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The stimulation electrodes 121 may be configured to emit the pulses in an outward radial direction proximate to or within a stimulation target. Additionally or alternatively, the stimulation electrodes 121 may be in the shape of a split or non-continuous ring such that the pulse may be directed in an outward radial direction adjacent to the stimulation electrodes 121. The stimulation electrodes 121 deliver high frequency and/or burst stimulation waveforms as described herein. The electrodes 121 may also sense ECAP signals and/or sensory action potential (SAP signals) during a data collection window. Optionally, the delivering operation may deliver the one stimulation waveform to a first sub-set of the electrodes and another stimulation waveform to a second sub-set of the electrodes, where the first and second sub-sets have at least one unique electrode relative to each other.

Optionally, the electrodes may include a microelectrode located immediately adjacent the select nerve fibers. The method may sense ECAP and/or SAP signals directly at the microelectrode and perform an iterative feedback loop to adjust at least one therapy parameter based on the Aδ, Aβ or C-fiber frequency components.

Throughout the embodiments described herein, the same electrodes 121 may be used for sensing and stimulation. Alternatively, one group of electrodes 121 may be used for sensing, while a different group of electrodes are used for stimulation. For example, the sensing electrodes 121 may be spaced apart along the lead from the stimulation electrodes. Optionally, the sensing electrodes 121 may be provided on a separate lead unique and distinct from the lead that includes the stimulation electrodes 121. For example, a conventional SCS lead may be positioned along the spinal column at a desired location in order to deliver therapy at one or more stimulation sites of interest, while a separate sensing lead is provided. As one example, electrodes 121 proximate the dorsal column may be used for stimulation, while separate electrodes proximate the dorsal root ganglion or dorsal root are used for sensing. As a further option, sensing electrodes may be located remote from the DRG or DR, such as along the dorsal column (DC), within the torso of the body and/or along the extremities of the patient, such as within the arms and legs. Optionally, the burst stimulation waveform may be delivered at electrodes proximate both of the dorsal column and the DRG, while sensing is performed at the DRG or DR.

When the electrodes are located along the DC, electrical fields can reach DR or tract of lissauer to activate A-delta and C fibers. For example when dermatomal fiber tract zone L1 needs to be activated for back pain, commonly stimulation electrodes may be located in T8-T10 where DR or the tract of lissauer is next the dermatomal fiber tract zone L1. Therefore ECAP from conventional SCS lead would sense from one or more of A-beta or A-delta or C fibers. Similarly, sensing electrodes located proximate to L1 or another lower vertebra may sense ECAP and/or SAP signals from the DR and/or DRG. Accordingly, a lead with electrodes proximate to the DC may practice the methods and systems described herein in connection with controlling stimulation parameters based on frequency decomposition.

In various embodiments herein, conventional SCS electrodes 121 and leads may be used for stimulation and/or sensing, provided that the SCS electrodes are configured to be located at a desired proximity relative to a target site or nervous tissue of interest. Additionally or alternatively, the lead to be used for sensing may include micro electrodes where the micro electrodes that are configured to be placed immediately adjacent fibers of interest, such as C-fibers, Aβ fibers and/or Aδ fibers. Additionally or alternatively, DC, DRG and/or DR leads/electrodes may be used along or in combination with micro-electrodes and/or SCS electrodes.

The lead 110 may comprise a lead body 172 of insulative material about a plurality of conductors within the material that extend from a proximal end of lead 110, proximate to the IPG 150, to its distal end. The conductors electrically couple a plurality of the stimulation electrodes 121 to a plurality of terminals (not shown) of the lead 110. The terminals are adapted to receive electrical pulses and the stimulation electrodes 121 are adapted to apply the pulses to the stimulation target of the patient. Also, sensing of physiological signals may occur through the stimulation electrodes 121, the conductors, and the terminals. It should be noted that although the lead 110 is depicted with four stimulation electrodes 121, the lead 110 may include any suitable number of stimulation electrodes 121 (e.g., less than four, more than four) as well as terminals, and internal conductors. Additionally or alternatively, various sensors (e.g., a position detector, a radiopaque fiducial) may be located near the distal end of the lead 110 and electrically coupled to terminals through conductors within the lead body 172.

Although not required for any embodiments, the lead body 172 of the lead 110 may be fabricated to flex and elongate upon implantation or advancing within the tissue (e.g., nervous tissue) of the patient towards the stimulation target and movements of the patient during or after implantation. By fabricating the lead body 172, according to some embodiments, the lead body 172 or a portion thereof is capable of elastic elongation under relatively low stretching forces. Also, after removal of the stretching force, the lead body 172 may be capable of resuming its original length and profile. Fabrication techniques and material characteristics for "body compliant" leads are disclosed in greater detail in U.S. Provisional Patent Application No. 60/788,518, entitled "Lead Body Manufacturing," which is expressly incorporated herein by reference.

Figure 2C:
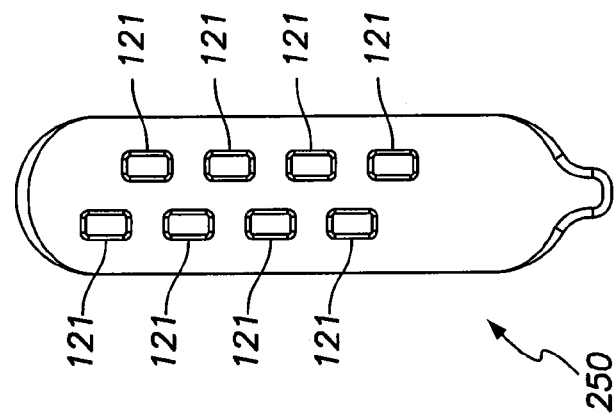
FIGS. 2A-2C depict stimulation portions for inclusion at the distal end of lead in accordance with embodiments herein.
Figure 2B:
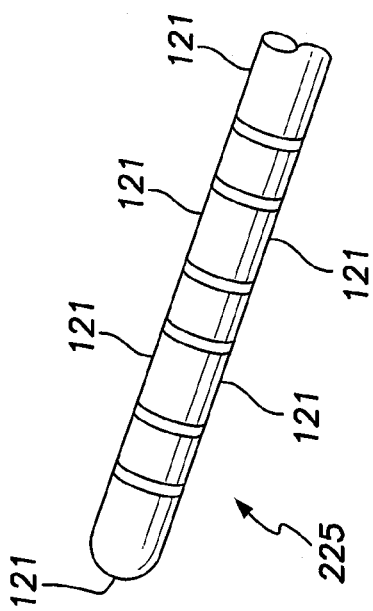
Figure 2A:
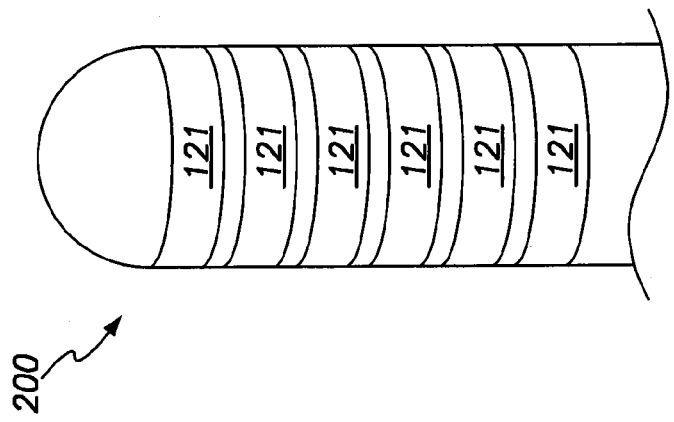

FIGS. 2A-2C respectively depict stimulation portions 200, 225, and 250 for inclusion at the distal end of lead 110. Stimulation portion 200 depicts a conventional stimulation portion of a "percutaneous" lead with multiple ring electrodes. Stimulation portion 225 depicts a stimulation portion including several segmented electrodes. Example fabrication processes are disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is incorporated herein by reference. stimulation portion 250 includes multiple planar electrodes on a paddle structure. Returning to FIG. 1, for implementation of the components within the IPG 150, a processor and associated charge control circuitry for an IPG is described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 156) of an IPG using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference.

An example and discussion of "constant current" pulse generating circuitry (e.g., pulse generating circuitry 152) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IPG 150. Different burst and/or high frequency pulses on different stimulation electrodes 121 may be generated using a single set of the pulse generating circuitry 152 using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., tonic stimulation waveform, burst stimulation waveform) that include generated and delivered stimulation pulses through various stimulation electrodes of one or more leads 121 as is also known in the art. Various sets of parameters may define the pulse characteristics and pulse timing for the pulses applied to the various stimulation electrodes 121. Although constant current pulse generating circuitry is contemplated for some embodiments, any other suitable type of pulse generating circuitry may be employed such as constant voltage pulse generating circuitry.

The controller 151 manages deliver of a stimulation waveform to at least one electrode located proximate to nervous tissue of interest. The stimulation waveform includes a series of pulses configured to excite at least one of Aβ, Aδ or C-fibers of the nervous tissue of interest. The controller 151 manages sensing of an ECAP or SAP signal from the nervous tissue of interest. The controller 151 analyzes a frequency content of the ECAP or SAP signal to obtain ECAP or SAP frequency data indicative of activity by at least one type of nerve fibers from a group comprising Aβ, Aδ and C fibers. The controller 151 determines the type of nerve fibers that were activated by the stimulation waveform based on the ECAP frequency data, or activated during the detection window by intrinsic neurologic inputs.

Optionally, the controller 151 may establish nerve fiber activation thresholds. To do so, the controller 151 iteratively repeats delivering and sensing operations for a group of test pulse parameter sets (TPPS). The controller 151 analyzes the ECAP signals, associated with each TPPS, to obtain frequency content data associated with the TPPS for the type(s) of nerve fibers of interest. The analyzing operations obtain a collection of frequency content data associated with the group of TPPS. The controller 151 establishes activation thresholds associated with each type of nerve fiber of interest.

The therapy parameters define at least one of a burst pattern, or high frequency stimulation waveforms. The controller 151 may determine whether a frequency content for each of the frequency components exceeds a threshold or falls within an acceptable range, thereby indicating that no pain or an acceptable low level of pain is experienced by the patient. The controller 151 repeats the delivering, sensing and adjusting operations to optimize the stimulation waveform. The analyzing operation may include analyzing a feature of interest from the ECAP/SAP pulse frequency, etc., and generating activity data based on the number of occurrences, average amplitude, pulse frequency, etc. of the feature of interest.

The controller 151 is configured to select a candidate TPS from the multiple therapy parameter sets based on a criteria of interest related to the action potential activity, and utilize the candidate TPS in connection with delivering therapy.

The controller 151 may identify an Aβ, C-fiber and/or Aδ frequency component of the ECAP signals. The controller 151 may adjust a burst frequency to reduce the C-fiber frequency component.

Memory 158 stores software to control operation of the controller 151 as explained herein. The memory 158 also stores ECAP signals, frequency content, activation information, SAP signals, therapy parameters, SAP activity level data, pain scales and the like. For example, the memory 158 may save ECAP or SAP activity level data for various different therapies as applied over a short or extended period of time. A collection of ECAP or SAP frequency content is accumulated for different therapies and may be compared to identify high, low and acceptable amounts of sensory activity for the Aβ, Aδ and/or C-fibers that result from different therapies. The memory 158 may store a pain-activity data relation defining a relation between high frequency content of the ECAP/SAP signals and pain scores indicative of pain experienced by a patient.

A controller device 160 may be implemented to charge/recharge the battery 154 of the IPG 150 (although a separate recharging device could alternatively be employed) and to program the IPG 150 on the pulse specifications while implanted within the patient. Although, in alternative embodiments separate programmer devices may be employed for charging and/or programming the NS system 100. The controller device 160 may be a processor-based system that possesses wireless communication capabilities. Software may be stored within a non-transitory memory of the controller device 160, which may be executed by the processor to control the various operations of the controller device 160. A "wand" 165 may be electrically connected to the controller device 160 through suitable electrical connectors (not shown). The electrical connectors may be electrically connected to a telemetry component 166 (e.g., inductor coil, RF transceiver) at the distal end of wand 165 through respective wires (not shown) allowing bi-directional communication with the IPG 150. Optionally, in some embodiments, the wand 165 may comprise one or more temperature sensors for use during charging operations.

The user may initiate communication with the IPG 150 by placing the wand 165 proximate to the NS system 100. Preferably, the placement of the wand 165 allows the telemetry system of the wand 165 to be aligned with the far-field and/or near field communication circuitry 155 of the IPG 150. The controller device 160 preferably provides one or more user interfaces 168 (e.g., touchscreen, keyboard, mouse, buttons, or the like) allowing the user to operate the IPG 150. The controller device 160 may be controlled by the user (e.g., doctor, clinician) through the user interface 168 allowing the user to interact with the IPG 150. The user interface 168 may permit the user to move electrical stimulation along and/or across one or more of the lead(s) 110 using different stimulation electrode 121 combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference.

Also, the controller device 160 may permit operation of the IPG 150 according to one or more therapies to treat the patient. Each therapy may include one or more sets of stimulation parameters of the pulse including pulse amplitude, pulse width, pulse frequency or inter-pulse period, pulse repetition parameter (e.g., number of times for a given pulse to be repeated for respective stimset during execution of program), biphasic pulses, monophasic pulses, etc. The IPG 150 modifies its internal parameters in response to the control signals from the controller device 160 to vary the stimulation characteristics of the stimulation pulses transmitted through the lead 110 to the tissue of the patient. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

Processes to Analyze ECAP/SAP Frequency Content

Figure 4:
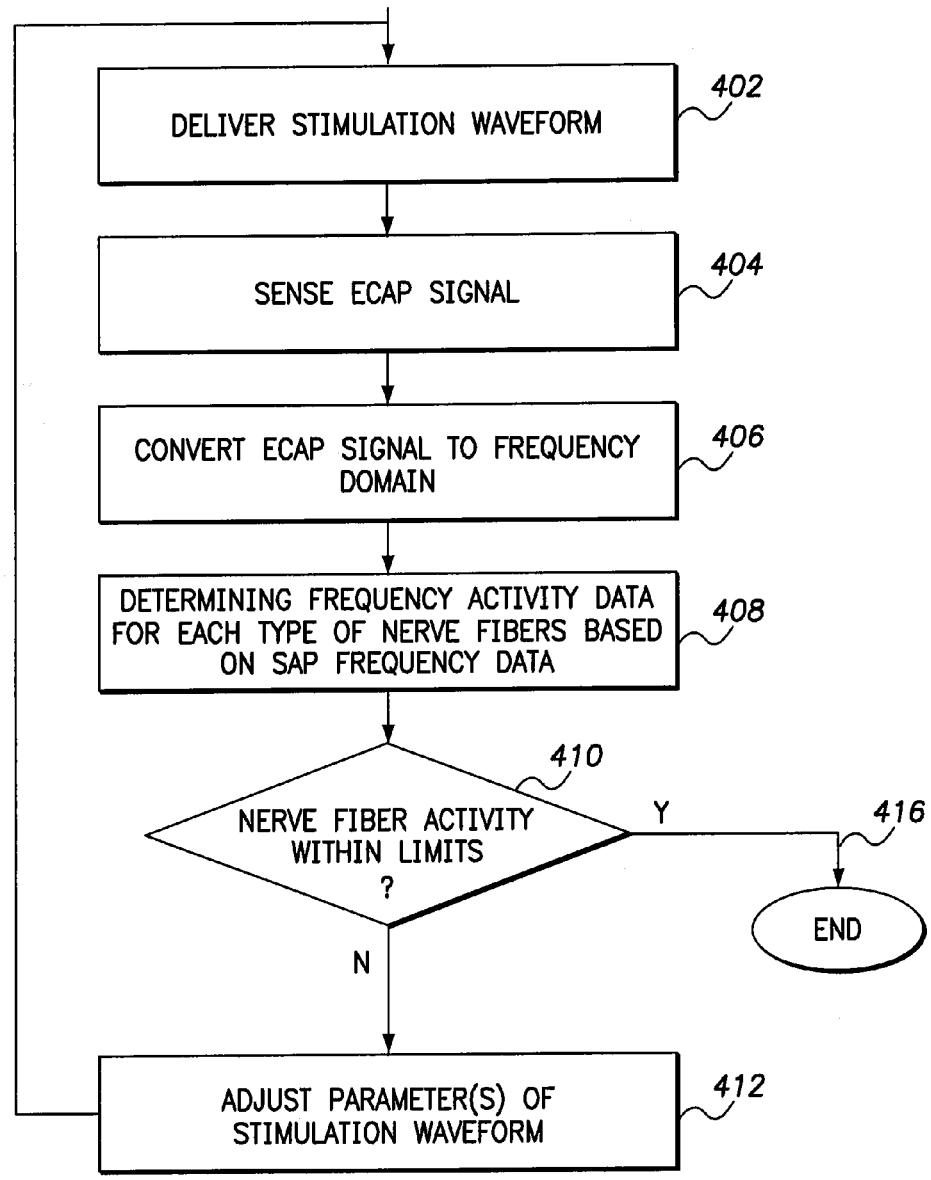
FIG. 4 illustrates a method to control stimulation of nervous tissue of a patient in accordance with embodiments herein.

FIG. 4 illustrates a method to control stimulation of nervous tissue of a patient in accordance with embodiments herein. The method of FIG. 4 controls DC, DR and DRG stimulation parameters based on frequency decomposition. The operations of FIG. 4 may be implemented by one or more processors, such as within an implantable pulse generator, external programmer, another external device and the like. The IPG, external programmer or other external device are coupled to a lead having at least one stimulation electrode that is implanted at a target position proximate to nervous tissue of interest. The operations of FIG. 4 are discussed below in connection with the illustrations of FIGS. 5A and 5B.

At 402, the method defines one or more stimulation waveform to be used. The stimulation waveform is defined by one or more parameters forming a therapy parameter set (TPS). The method delivers a stimulation waveform to at least one electrode located proximate to nervous tissue of interest. The stimulation waveform includes a series of pulses configured to excite at least one of Aβ, Aδ or C-fibers of the nervous tissue of interest. The stimulation waveform is defined by therapy parameters. For example, the therapy parameters may define at least one of a burst stimulation waveform or a high frequency stimulation waveform. Examples of therapy parameters within a TPS include, but are not limited to pulse amplitude, pulse width, interpulse delay, number of pulses per burst, pulse frequency, burst frequency, etc. The TPS is defined such that the stimulation waveform is configured to excite a select one or more of Aβ fibers, Aδ fibers and/or C-fibers at the target position. As another example, the TPS may define a stimulation waveform that does not achieve a desired impact. For example, the TPS may not excite a select one or more of the Aβ fibers, Aδ fibers and/or C-fibers at all or sufficiently.

As explained herein, the stimulation waveform may represent a baseline stimulation waveform or a fiber-targeted stimulation waveform. Baseline stimulation waveforms are delivered to collect baseline activity data in connection with various types of nerve fibers. The baseline activity data may be derived from baseline ECAP signals sensed in response to a baseline stimulation waveform. The baseline activity data may also be derived from sensory action potential (SAP) signals that are generated in response to intrinsic neurologic behavior, such as in response to a predetermined externally induced physical inputs (e.g. a pinch, scratch, touch, noxious input, exposure to high or low temperature and the like). The SAP signals may be collected during a detection window following delivery of a stimulation waveform after passage of any ECAP signals associated with the stimulation waveform. Thus, the SAP signals are not directly responsive to the stimulation waveforms, but instead are representative of intrinsic neurologic behavior during a detection window following a stimulation waveform. The methods and systems described herein are generally discussed in connection with sensing and analyzing ECAP signals. However, it should be understood that the methods and systems are equally applicable to sensing and analyzing SAP signals during detection windows following stimulation waveforms.

At 404, the method senses an evoked compound action potential (ECAP) signal from the nervous tissue of interest. The ECAP signal represents ECAP recorded activity from afferent neurons carrying both painful stimuli, within the Aδ and C fibers, and non-painful stimuli, within the Aβ fibers.

At 406, the method performs frequency decomposition by analyzing a frequency content of the ECAP signal to obtain ECAP frequency data indicative of activity by at least one type of nerve fiber from a group comprising Aβ, Aδ and C fibers. For example, the decomposition/analyzing operation may include using a fast Fourier transform to convert the ECAP signal to a frequency domain to generate the ECAP frequency data which includes clusters of frequency domain components distributed along a frequency spectrum, where each of the clusters is associated with one of the Aβ, Aδ and C nerve fibers.

Figure 5:
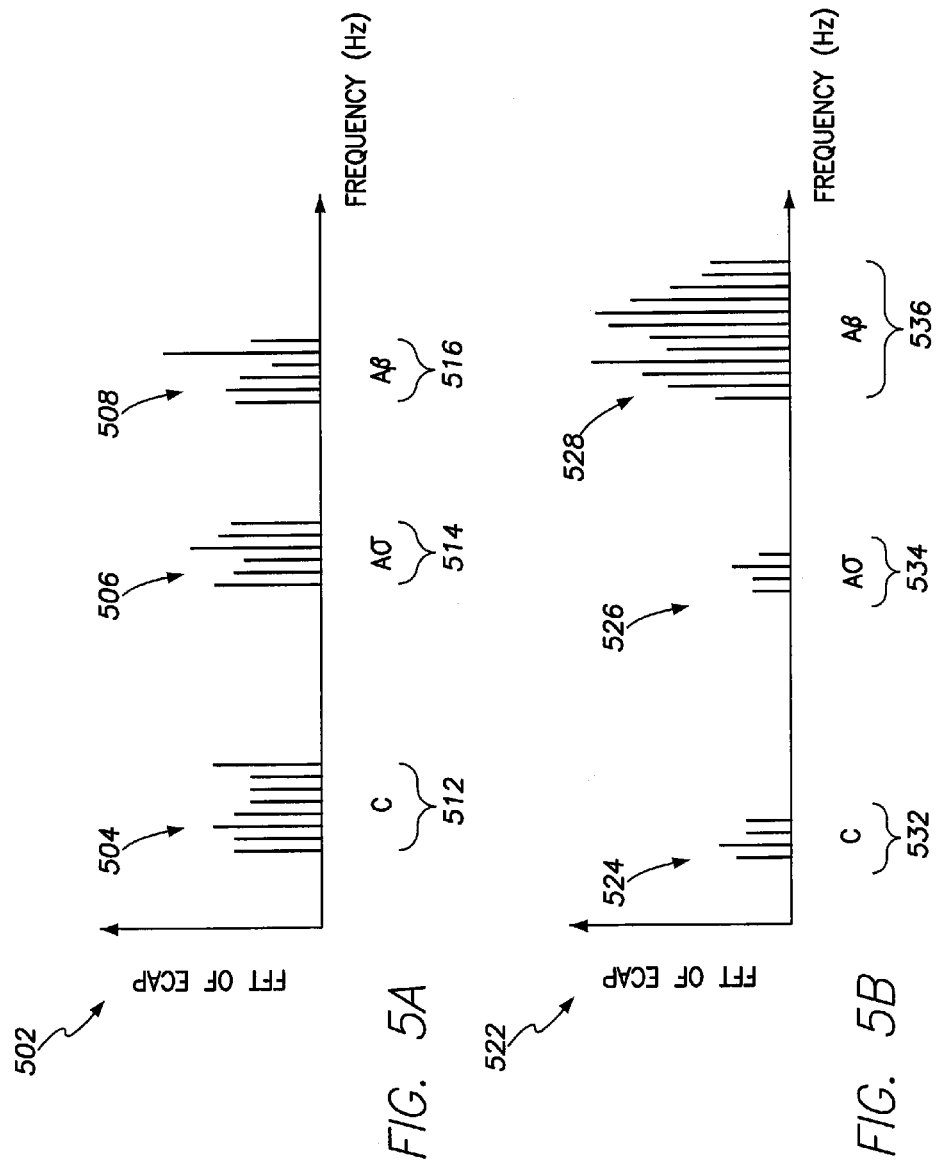
FIG. 5A illustrates a frequency spectrum where the horizontal axis corresponds to individual frequencies (or frequency bin) and the vertical axis corresponds to the amount or amplitude of frequency content (after an FFT) associated with each individual frequency (or frequency bin) in accordance with embodiments herein.
FIG. 5B illustrates an example of a frequency spectrum that is generated, when applying an FFT analysis, to an ECAP signal that is produced in response to a stimulation waveform that has been set to target stimulation of the Aβ fibers in accordance with embodiments herein.

With reference to FIG. 5A, a frequency spectrum 502 is illustrated where the horizontal axis corresponds to individual frequencies (or frequency bin) and the vertical axis corresponds to the amount or amplitude of frequency content associated with each individual frequency (or frequency bin). The frequency spectrum 502 is associated with an ECAP signal sensed over a predetermined window or period of time. For example, the ECAP signal may be sensed for a select window having a width of a few hundreds of microseconds. The frequency spectrum 502 may represent the fast Fourier transform of an individual window of ECAP signals, or alternatively ECAP signals collected during multiple sensing windows.

The frequency spectrum 502 includes ECAP frequency data that comprises a C fiber component 504, an Aδ fiber component 506 and an Aβ fiber component 508. Each of the components 504-508 comprise individual frequency bins grouped closely with one another in ranges along the frequency spectrum, where the individual frequency bins have associated different amplitudes. The fast Fourier transform converts the ECAP signals to ECAP frequency data that is separated into distinct frequency clusters 512-516 associated with frequency domain components 504-508, where each of the clusters 512-516 has a separate and distinct frequency range. For example, the cluster 512 (associated with the C fiber component 504) may be located in a lower frequency range, while the cluster 514 (associated with the Aδ fiber component 506) is located in a central frequency range, and the cluster 516 (associated with the Aβ fiber component 508) is located in a higher frequency range (the terms lower, central and higher being relative to one another).

Each of the clusters 512-516 has an associated amount of frequency activity data. For example, each frequency bin or factor within a cluster has a corresponding amplitude of the signal associated with the frequency bin/factor. The frequency activity data associated with an individual cluster 512-516 may be calculated in various manners. For example, the frequency activity data activity for any one of the clusters 512-516 may correspond to an average amplitude of the frequency bins therein, or alternatively, the frequency activity data may be defined by summing the activity levels for each of the frequency bins in the corresponding cluster 512-516 (e.g., integrating the energy within the cluster). Optionally, other mathematical factors may be used to define the frequency activity data associated with each fiber frequency component 504-508.

In the example of FIG. 5A, the fiber frequency components 504-508 exhibit relatively common or similar amounts of action potential (AP) activity when compared to one another. As an example, the ECAP frequency content 502 of FIG. 5A may correspond to a baseline ECAP signal generated in response to a baseline stimulation waveform. The baseline stimulation waveform has not yet been adjusted to focus activation upon a select one or more of the types of nerve fibers. In accordance with embodiments herein, the parameters of the stimulation waveform are adjusted such that the activity within a select one or more of the components 504-508 increases, while the activity within non-select components 504-508 decreases.

FIG. 5B illustrates an example of a frequency spectrum 522 that is generated, when applying an FFT analysis, to an ECAP signal that is produced in response to a fiber targeted stimulation waveform. A fiber targeted stimulation waveform has been set to target stimulation of a select fiber such as the Aβ fibers. The frequency spectrum 522 includes a C fiber frequency component 524, an Aδ fiber frequency component 526 and an Aβ fiber frequency component 528. The frequency components 524, 526 and 528 are separated from one another and distributed along the frequency spectrum within clusters 532-534. The C and Aδ fiber frequency components 524, 526 include a relatively small amount of action potential activity, as compared to the larger amount of action potential activity exhibited by the Aβ fiber frequency component 528. The Aβ fiber frequency component 528 has a larger amount of action potential activity due to the Aβ fiber targeted stimulation waveform that was used to generate the ECAP signal.

Returning to FIG. 4, at 408, the method determines the type of nerve fibers that were activated by the stimulation waveform based on the ECAP frequency data. For example, the determining operation may identify an amount of activity exhibited by the frequency bins or factors in one or more of the C, Aδ and Aβ fiber components 504-508. In the example of FIG. 5A, the determination would indicate that a somewhat equal amount of activity is exhibited by each of the components 504-508. In the example of FIG. 5B, the determination would indicate that the Aβ fiber component 536 exhibits a substantially larger amount of action potential activity than in components 524 and 526.

At 410, the method determines whether the amount of action potential activity associated with each frequency component is within an acceptable range or level. For example, the method may establish, as a threshold or criteria, that the action potential activity associated with the Aδ fiber component 536 should include at least a select amount of total energy, or have at least one frequency bin with a peak amplitude that exceeds a select peak amplitude, or include at least a select amount of average energy. As another option, the threshold or criteria may indicate that the action potential activity include at least a select number of frequency bins that have signals with at least a select amplitude. Other thresholds or criteria may be used to determine whether an amount of action potential activity associated with a target fiber is sufficient. As noted above in connection with FIG. 5A, the frequency content is grouped into clusters 512-516. For example, the activity distribution illustrated in FIG. 5A may be determined at 408. However, the method may desire less activity within the clusters 512, 514 associated with the C fibers and Aδ fibers. When the activity associated with each frequency range is acceptable, flow moves along path for 416 and the process ends. Otherwise, flow moves to 412.

At 412, the method adjusts at least one of the therapy parameters to change the stimulation waveform based on the ECAP frequency data. The adjusting operation may adjust the stimulation parameters based on the clusters 512-516 of frequency domain components 504-508 to maintain a select amount of activation for a select one or more of the types of nerve fibers based on the determination at 410. For example, when it is desirable to increase the amount of action potential activity associated with the Aβ fibers, the parameters may be adjusted to increase the pulse width and increase the pulse amplitude. When it is desirable to increase the amount of action potential activity associated with the C fibers, the parameters may be adjusted to increase the pulse frequency. Additionally or alternatively, the type of stimulation waveform may be changed, such as adding burst of stimulation or switching to high frequency stimulation to activate Aβ fibers while avoiding activation of Aδ and C fibers. As another alternative, a random pulse patterns may be utilized. In a random pattern, multiple different types of waveforms are used, with a $1^{st}$ type of waveform used in a $1^{st}$ segment of the pattern and a different type of waveform used in a $2^{nd}$ segment of the pattern, and the like. As an example, a $1^{st}$ segment may deliver pulses in a $1^{st}$ frequency, while a $2^{nd}$ segment of a pulse pattern may deliver pulses at a $2^{nd}$ different frequency. As a further example, the pulse to pulse interval may be varied as another parameter.

The pulse width, pulse frequency, number of pulses and/or pulse amplitude of the stimulation waveform are only example of the parameters that may be increased or decreased when a particular frequency component within the frequency spectrum does not exhibit sufficient AP activity (e.g. an amount of activity that exceeds a minimum threshold) or exhibit excessive activity.

In some embodiments, the adjusting operation may select between a burst, high frequency, tonic or random pattern stimulation waveforms based upon which of the burst, high frequency, tonic or random pattern stimulation waveforms results in a selected level of AP activation for a target one or more of the Aβ, Aδ or C fibers. As an example, it may be determined that a tonic stimulation waveform yields a desired amount of activity in the Aβ fibers, while a high frequency stimulation waveform may yield a desired amount of activity in the C fibers.

Figure 6:
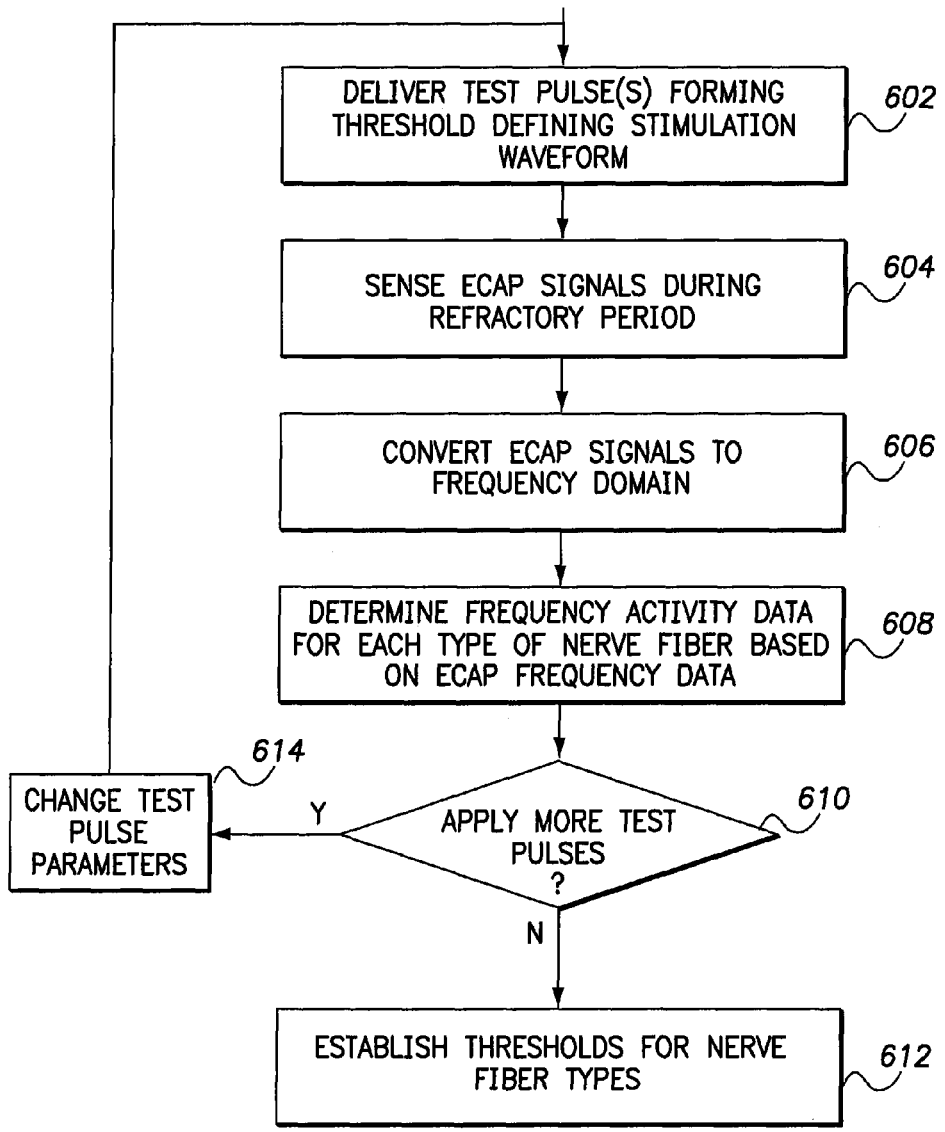
FIG. 6 illustrates a method for defining thresholds for activating at least one of the Aβ, Aδ or C fibers in accordance with embodiments herein.

FIG. 6 illustrates a method for defining thresholds for fiber targeted AP activation of at least one of the Aβ, Aδ or C fibers in accordance with embodiments herein. The thresholds are defined based on the ECAP frequency data and the stimulation waveform.

At 602, the method delivers a threshold defining stimulation waveform comprised of one or more test pulses. At 604, the method senses an evoked compound action potential signal from the nervous tissue of interest. At 606, the method analyzes a frequency content of the ECAP signal to obtain ECAP frequency data indicative of AP activity by at least one type of the nerve fiber in response to the test pulses. At 608, the method determines the type(s) of nerve fibers that were activated by the stimulation waveform based on the ECAP frequency data and the amount of AP activity exhibited with each type of nerve fiber. At 608, the method stores the AP activation information associated with each type of nerve fiber, along with the parameters defining the corresponding test pulse, in response to which the ECAP signal was produced.

At 610, the method determines whether additional test pulses should be applied in order for more ECAP frequency data to be collected. When the method determines that a sufficient amount of ECAP frequency data has been collected and a sufficient number of threshold defining stimulation waveforms have been applied, flow moves to 612. Otherwise, flow moves to 614.

At 612, the method adjusts at least one of the therapy parameters, defining the tests pulse(s), to change the stimulation waveform, and the operations of 602-610 are repeated.

At 614, the method establishes one or more thresholds in connection with excitation of the Aβ, Aδ or C fibers based on the frequency domain components in the ECAP frequency data collected over multiple iterations through 602-614.

For example, with reference to FIG. 5A, the method may analyze the frequency spectrum 502 and identify the upper and lower limits of each cluster 512-516. From the upper and lower limits, the method may determine an acceptable range associated with each frequency component 504-508. The method may further analyze the signal amplitude associated with each frequency bin within each cluster 512-516 to determine an amount of AP activity associated with each cluster 512-516. The amount of AP activity, frequency range and other characteristics defining each of the clusters 512-516 may be recorded and characterized in various manners. For example, the AP activity, frequency range and other characteristics associated with the clusters 512-516 may be recorded as thresholds associated with an excessive amount of AP activity for nerve fibers for which it is desirable to avoid activation (e.g. non-target nerve fibers). Hence, measurement recorded in connection with the frequency spectrum 502 may be utilized to define thresholds and criteria for activation levels that are not acceptable during operation and, when present, warrant changes in the stimulation waveform.

As a further example, with reference to FIG. 5B, when the frequency spectrum 522 is analyzed at 614, the method may record the amount of AP activity associated with cluster 536 to represent one or more thresholds indicative of an acceptable amount of AP activity for a targeted fiber. For example, the method may identify characteristics for an acceptable cluster, such as the upper and lower frequency limits associated with cluster 536, as well as the total AP activity, average AP activity maximum peak signal and its standard deviation in connection with one or more frequency bins, and the like. The AP activity, frequency range and other characteristics associated with the cluster 536 may be recorded as thresholds associated with an acceptable amount of AP activity for a nerve fiber that it is desirable to activate (e.g. a target nerve fiber).

Each type of nerve fiber may have different thresholds associated with AP activity, frequency range and the like for target and nontarget nerve fibers. For example, the C fibers may have target and nontarget thresholds indicating acceptable amounts of AP activity, frequency range and the like for when the C fibers are targeted (e.g. should exhibit activity) or are not targeted (e.g. should not exhibit activity). The a beta and a Delta fibers similarly have target and nontarget thresholds indicative of acceptable and unacceptable amounts of AP activity, frequency range and the like for when such fibers are targeted or not targeted.

Figure 7:
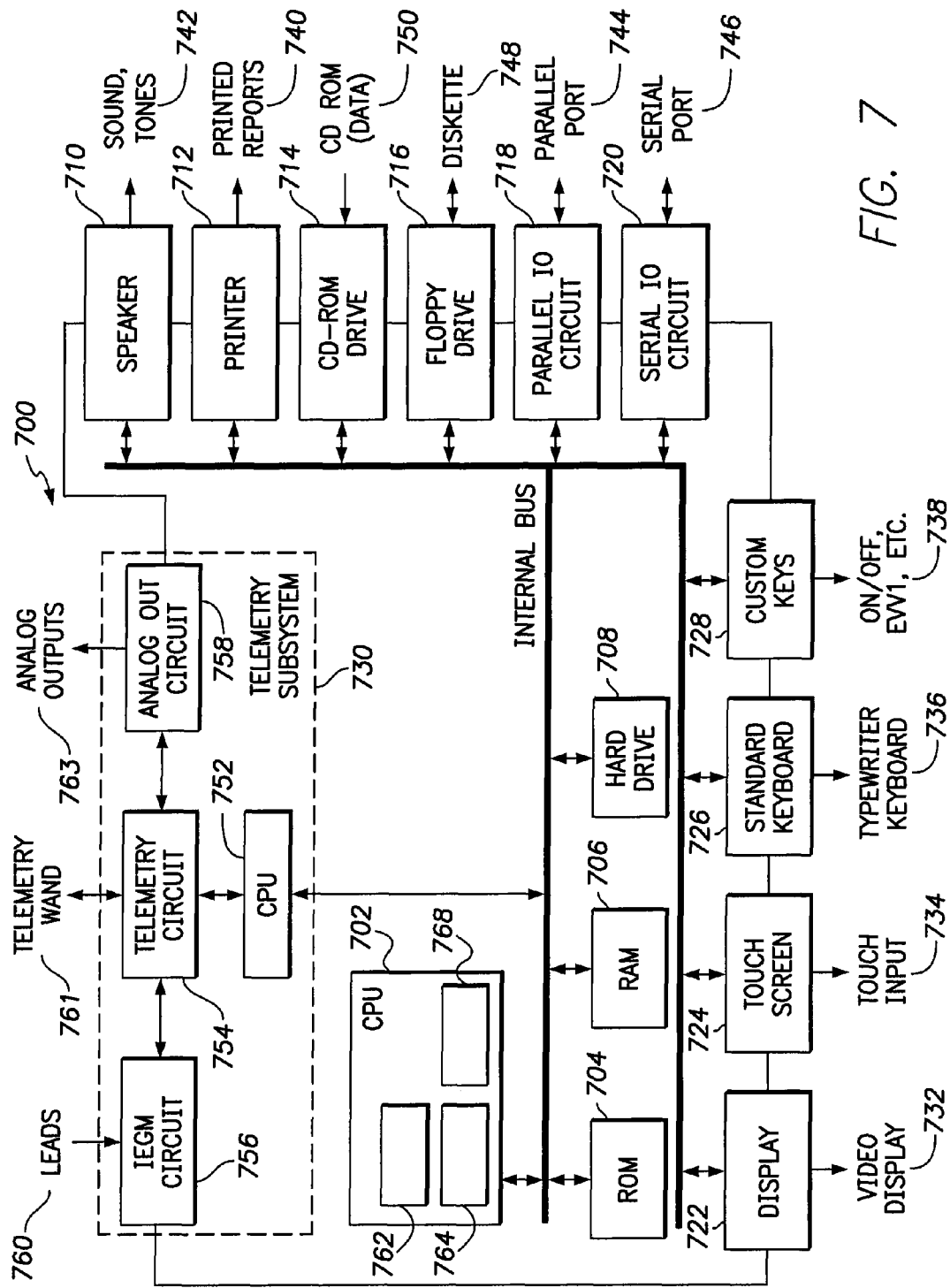
FIG. 7 illustrates a functional block diagram of an embodiment of an electronic control unit that is operated in accordance with the processes described herein.

FIG. 7 illustrates a functional block diagram of an embodiment of an electronic control unit (ECU) 700 that is operated in accordance with the processes described herein to analyze ECAP and/or SAP signals and to interface with one or more IPGs and/or leads with electrodes positioned at stimulation sites to deliver coupled tonic/burst therapies and/or sense sensory action potential signals. The ECU 700 may be a workstation, a portable computer, a PDA, a cell phone and the like. The ECU 700 includes an internal bus that connects/interfaces with a Central Processing Unit (CPU) 702, ROM 704, RAM 706, a hard drive 708, the speaker 710, a printer 712, a CD-ROM drive 714, a floppy drive 716, a parallel I/O circuit 718, a serial I/O circuit 720, the display 722, a touch screen 724, a standard keyboard connection 726, custom keys 728, and a telemetry subsystem 730. The internal bus is an address/data bus that transfers information between the various components described herein. The hard drive 708 may store operational programs as well as data, such as waveform templates and detection thresholds.

The CPU 702 typically includes a microprocessor, a micro-controller, or equivalent control circuitry, and may interface with an IPG and/or lead. The CPU 702 may include RAM or ROM memory, logic and timing circuitry, state machine circuitry, and I/O circuitry to interface with the IPG and/or lead. The display 722 (e.g., may be connected to the video display 732). The touch screen 724 may display graphic information relating to the CNS 110. The display 722 displays various information related to the processes described herein. The touch screen 724 accepts a user's touch input 734 when selections are made. The keyboard 726 (e.g., a typewriter keyboard 736) allows the user to enter data to the displayed fields, as well as interface with the telemetry subsystem 730. Furthermore, custom keys 728 turn on/off 738 (e.g., EVVI) the ECU 700. The printer 712 prints copies of reports 740 for a physician to review or to be placed in a patient file, and speaker 710 provides an audible warning (e.g., sounds and tones 742) to the user. The parallel I/O circuit 718 interfaces with a parallel port 744. The serial I/O circuit 720 interfaces with a serial port 746. The floppy drive 716 accepts diskettes 748. Optionally, the floppy drive 716 may include a USB port or other interface capable of communicating with a USB device such as a memory stick. The CD-ROM drive 714 accepts CD ROMs 750.

The CPU 702 is configured to analyze ECAP/SAP signals collected by one or more electrodes. The CPU 702 includes a therapy circuit module 764 that is configured to control delivery of stimulation waveforms.

The CPU 702 also includes an ECAP analysis circuit module 768 that receives ECAP or SAP signals from at least one electrode on the lead, and analyzes the ECAP/SAP signals in the frequency domain as explained herein.

The telemetry subsystem 730 includes a central processing unit (CPU) 752 in electrical communication with a telemetry circuit 754, which communicates with both an SAP circuit 756 and an analog out circuit 758. The circuit 756 may be connected to leads 760. The circuit 756 may also be connected to implantable leads to receive and process SAP signals. Optionally, the SAP signals sensed by the leads may be collected by the CNS 110 and then transmitted, to the ECU 700, wirelessly to the telemetry subsystem 730 input.

The telemetry circuit 754 is connected to a telemetry wand 761. The analog out circuit 758 includes communication circuits to communicate with analog outputs 763. The ECU 700 may wirelessly communicate with the CNS 110 and utilize protocols, such as Bluetooth, GSM, infrared wireless LANs, HIPERLAN, 3G, satellite, as well as circuit and packet data protocols, and the like. Alternatively, a hard-wired connection may be used to connect the ECU 700 to the CNS 110.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) are hardwired to perform the methods or portions of the methods described herein, and/or when the processors (e.g., of the devices described herein) operate according to one or more software programs that are written by one or more persons of ordinary skill in the art to perform the operations described in connection with the methods.

The controller may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the controllers and the controller device may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The controllers and the controller device may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein.

The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

Figure 8:
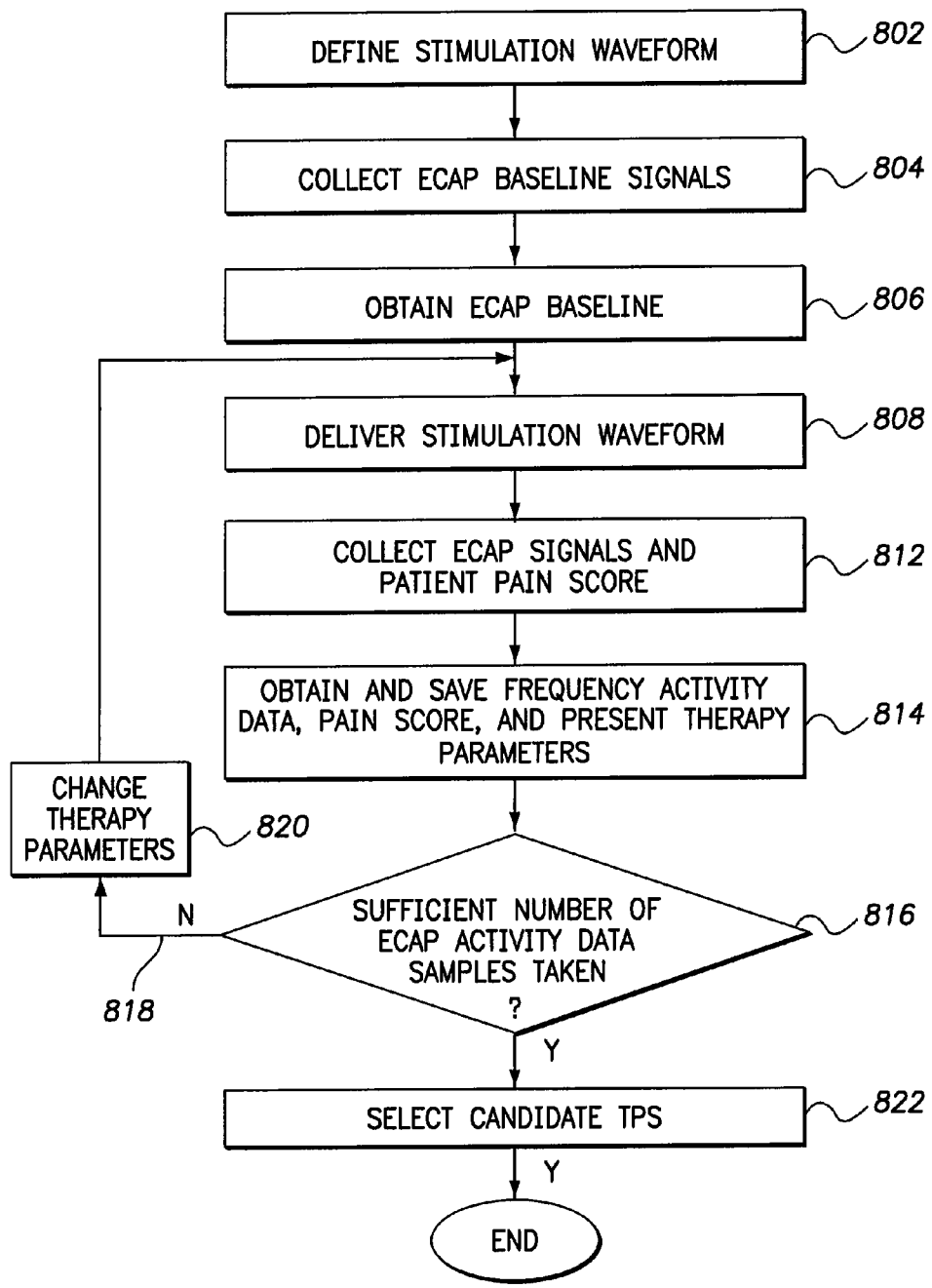
FIG. 8 illustrates a process for collecting and analyzing activity data in connection with multiple therapy parameter sets in accordance with embodiments herein.

FIG. 8 illustrates a process for collecting and analyzing frequency activity data in connection with multiple therapy parameter sets in accordance with embodiments herein. At 802-806, the method establishes a baseline. At 802, the method defines one or more stimulation waveform to be used. The stimulation waveform is defined by one or more parameters forming a therapy parameter set (TPS).

At 804, the method senses ECAP baseline signals by collecting SAP/ECAP signals, for a detection window The ECAP baseline signal is described herein. The ECAP baseline signals, collected over a single data collection window, represent an ECAP baseline sample for a single time interval, where the ECAP baseline sample is indicative of a baseline responsiveness of the fibers of interest (C-fibers and/or Aδ fibers), such as when baseline sensory stimulation is delivered.

Optionally, an SAP baseline signal may be collected. The SAP baseline signals are indicative of the sensory action potential experienced naturally or inherently by nervous tissue of interest at the target position.

At 806, the ECAP baseline sample is converted through an FFT to the frequency domain to generate ECAP frequency data. The ECAP frequency data is analyzed for baseline features, such as clusters of frequency bins within separate and distinct frequency ranges and having corresponding AP activity and/or signal amplitude associated with each frequency bin. Herein, the frequency locations and frequency ranges associated with each cluster, and the amplitudes of the frequency bins therein are generally referred to as a frequency distribution morphology of the ECAP frequency data. At 806, the method analyzes the frequency distribution morphology, such as a number of frequency bins in each cluster, an amplitude of peaks, a number of peaks, a variation in frequency peaks and the like within the ECAP frequency data to determine baseline activity information associated with each type of nerve fiber of interest. The ECAP baseline sample(s), the baseline activity information, ECAP frequency data, corresponding TPS and other information are stored in memory. The ECAP baseline activity information may be used over time as a reference for comparison with later collected ECAP samples. Optionally, the operations at 804 and 806 may be omitted entirely.

At 808, the method delivers the stimulation waveform to at least one electrode based on the TPS defined at 802. The stimulation waveform is delivered to at least one stimulation electrode on the lead. The stimulation waveform may represent a series of monophasic pulses (with a positive or negative current pulse) or a series of biphasic waveform (with positive and negative pulses) or other shaped waveforms. When the stimulation waveform is biphasic, a first pulse phase may be configured to capture at least a portion of the Aβ fibers, A-delta fibers and/or C-fibers, while the second pulse phase is configured to repolarize charge at a stimulation site. By repolarizing charge at the stimulation site, the second pulse phase limits an extent of Aβ fiber, Aδ fiber and/or C-fiber excitation (e.g., a degree to which, or amount of, the fibers of interest are excited).

At 812, the method senses ECAP signals and collects the ECAP signals for a data collection window. The ECAP signals, collected over a single detection window, represent an ECAP sample for a single time interval. The ECAP signals are saved as an SAP/ECAP sample.

At 812, optionally, the patient may enter a pain score to indicate an amount/degree of pain experienced by the patient relative to a predetermined pain index.

At 814, the ECAP sample is converted through an FFT to the frequency domain to generate ECAP frequency data. The ECAP frequency data is analyzed for features of interest, such as clusters of frequency bins within separate and distinct frequency ranges and having corresponding signal amplitude associated with each frequency bin. The method analyzes the ECAP frequency data to obtain activity data associated with the TPS. The activity data corresponds to activity for the fiber of interest, such as at least one of the ECAP A-fiber components, ECAP C-fiber components and/or ECAP Aδ fiber components. The analysis at 814 is repeated numerous times to obtain a collection of activity data associated with a group or multiple TPS. In the embodiment illustrated in FIG. 8, the operation at 814 may be implemented during each iteration through the operation at 808-820. Optionally, the operation at 814 may be implemented once after an entire collection of activity data is obtained from a predetermined number of iterations through the operations at 808-820 for the group or multiple different combinations of therapy parameters.

At 814, the method also saves the pain score, and frequency activity data along with the values for the corresponding therapy parameter set, such as in a memory of the IPG, external programmer or other external device. The activity data, pain scores and the associated therapy parameter set are saved, over time, in connection with delivering therapy based on multiple therapy parameter sets, thereby developing a therapy/sensitivity history for the patient.

At 816, the method determines whether a sufficient number of ECAP samples have been collected (and analyzed). When a sufficient number of ECAP samples have been collected, flow moves to 822. When it is determined that additional ECAP samples should be collected, flow moves along 818 to 820.

At 820, the method changes a value for one or more of the parameters within the therapy parameter set. The change at 820 may be performed in a predetermined systematic stepwise manner. For example, each parameter within the therapy parameter set may be incrementally adjusted by a select amount during separate iterations through the operations at 808-816. As an example, during iterations 1-8, the method may only change the amplitude of the stimulation waveform between low, medium and high amplitudes, while maintaining constant all other parameters within the TPS. After cycling through each of the pulse amplitudes of interest, the pulse amplitude may be reset to the low level for iterations 4-6, during which the pulse width is changed from short to medium to long. During iterations 7-9, the pulse amplitude may be set to the medium level, while the pulse width is again changed from short to medium to long, while all other parameters are maintained constant. The foregoing process may be repeated until each, or at least a select portion, of the potential permutations and combinations of levels for the parameters are used during the operations at 808-816 to form the group of TPS for which the collection of activity data is accumulated.

Alternatively or additionally, not all permutations and combinations of parameter levels may be used. For example, a physician or other user may select (and/or program) individual TPS of interest to be tested as the group of TPS. For example, the operations at 808-816 may only be repeated for 5 to 10 or 20 different TPS, even though many more permutations and combinations of levels for the various parameters exist. The change performed at 820 may be based on pre-stored settings or may represent an input from a physician or other user during operation.

Optionally, the amount of change during each iteration through 820 may vary, such as with larger step changes made during initial iterations and smaller step changes made during later iterations. Optionally, the amount of change at 820 may be based on a difference between the activity data and the threshold. For example, when the activity data substantially exceeds the threshold, larger changes may be applied to one or more parameters at 820. As the difference between the activity data and threshold decreases, the incremental change in the one or more parameters is changed by similarly/proportionally decreasing amounts. Following 820, flow returns to 808.

The operations at 808-316 build a database, file, or generally a pain-activity data relation corresponding to a relation between high frequency content of the ECAP signals and pain scores indicative of a level of pain experienced by the patient.

At 822, the method selects a candidate TPS from the multiple or group of TPS based on one or more criteria of interest. For example, when the criteria of interest represents a threshold or predetermined range for the activity data, the candidate TPS may be selected as the TPS that resulted in activity data that satisfy the threshold or predetermined range. For example, when the criteria of interest represents sensory activity, at 822, the method may identify the ECAP sample for which the lowest or smallest amount of activity data was identified. The lowest or smallest amount of activity is measured relative to the activity data of the other ECAP samples. The method cross references ECAP sample, that exhibits the lowest or smallest amount of activity data, to the corresponding therapy parameter set which is designated as the candidate TPS. As one example, the selection at 822 may seek to optimize the candidate TPS to define as a burst stimulation waveform that affords an ECAP activity below a threshold or within a range, collectively referred to as a result of interest, without inducing paresthesia. Once a candidate TPS is selected, the candidate TPS is used for subsequent therapy for a period of time, for example until it becomes desirable to repeat the process of FIG. 8A to determine a new candidate TPS.

The operations at 808-820 may be repeated for a number of different therapy parameter sets. For example, it may be desirable to obtain activity data in connection with 5, 10 or more than 10 different stimulation waveforms, in order to derive a more complete understanding of a particular patient's neural fiber activity respond to different stimulation waveforms. When a sufficient amount of activity data (e.g. enough ECAP samples) is collected, the process ends and the candidate TPS is selected and implemented.

The operations at 808-820 are iteratively repeated to form a feedback loop in which the therapy parameter set is continuously updated until obtaining a burst stimulation waveform that inhibits spontaneous action potentials along the slow conduction fibers to no more than a select amount of activity.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f), unless and until such claim limitations expressly use the phrase "means for" followed by a statement of function void of further structure.

What is claimed is:

1. A method to control stimulation of nervous tissue of a patient to treat chronic pain in a patient, the method comprising:
   delivering one or more stimulation waveforms to at least one electrode located proximate to a dorsal root ganglion, the one or more stimulation waveforms including a series of pulses configured to excite A-beta (Aβ) fibers, A-delta (Aδ) fibers and C-fibers of the dorsal root ganglion, the one or more stimulation waveforms defined by therapy parameters;
   sensing an evoked compound action potential (ECAP) signal from the dorsal root ganglion;
   analyzing a frequency content of the ECAP signal to obtain ECAP frequency data indicative of activity by Aβ, Aδ and C fibers; and
   determining the type of nerve fibers that were activated by the one or more stimulation waveforms based on the ECAP frequency data;
   delivering stimulation pulses to the dorsal root ganglion to treat chronic pain of patient according to therapy parameters, selected in response to the determining, that activate Aβ fibers and reduce activation of Aδ and C fibers.

2. The method of claim 1, wherein the ECAP frequency data includes Aβ, Aδ and C fiber components, the determining operation identifying an amount of activity exhibited by at least one of the Aβ, Aδ and C fiber components in response to the one or more stimulation waveforms.

3. The method of claim 1, wherein the analyzing operation includes using a fast Fourier transform to convert the ECAP signal to a frequency domain, the ECAP frequency data including clusters of frequency domain components distributed along a frequency spectrum, where each of the clusters is associated with one of the Aβ, Aδ and C nerve fibers.

4. The method of claim 1, wherein the ECAP signal represents ECAP recorded activity from afferent neurons carrying both painful stimuli, within the Aδ and C fibers, and non-painful stimuli, within the Aβ fibers.

5. The method of claim 1, further comprising adjusting at least one of the therapy parameters based on the ECAP frequency data.

6. The method of claim 5, wherein the adjusting operation selects between a burst, high frequency, tonic or random pattern stimulation waveforms based upon which of the burst, high frequency, tonic or random pattern stimulation waveforms results in a selected level of activation for a target one or more of the Aβ, Aδ or C fibers.

7. The method of claim 5, wherein the analyzing operation uses a fast Fourier transform on the ECAP signals to define clusters of frequency domain components within the ECAP frequency data, the adjusting operation adjusting the stimulation parameters based on the clusters of frequency domain components to maintain a select amount of activation of a select one or more of the types of nerve fibers.

8. The method of claim 1, further comprising defining thresholds for activating at least one of the Aβ, Aδ or C fibers based on the ECAP frequency data and the one or more stimulation waveforms.

9. The method of claim 1, wherein the one or more stimulation waveforms are delivered with a collection of test pulses having at least one of different amplitudes and pulse widths, the method further comprising establishing thresholds in connection with excitation of the Aβ, Aδ or C fibers based on first detection of frequency domain components in the ECAP frequency data indicating activity of the corresponding Aβ, Aδ or C fibers.

10. The method of claim 1, wherein the therapy parameters define at least one of a burst stimulation waveform or a high frequency stimulation waveform.

* * * * *